United States Patent [19]

Buchholz

[11] 4,279,041
[45] Jul. 21, 1981

[54] ENDOPROSTHESIS COMPOSED OF A SOCKET AND A HEAD RECEIVABLE AND LOCKABLE IN THE SOCKET

[76] Inventor: Hans-Wilhelm Buchholz, Möwenstrasse 12, 2000 Hamburg 60, Fed. Rep. of Germany

[21] Appl. No.: 54,895

[22] Filed: Jul. 5, 1979

[30] Foreign Application Priority Data

Jul. 6, 1978 [DE] Fed. Rep. of Germany ....... 2829676

[51] Int. Cl.³ .............................................. A61F 1/03
[52] U.S. Cl. .............................. 3/1.912; 128/92 CA; 403/123; 403/353
[58] Field of Search ........................ 3/1.9, 1.91, 1.911, 3/1.912, 1.913; 128/92 C, 92 CA; 403/353, 122, 123; 29/149.5 B

[56] References Cited

U.S. PATENT DOCUMENTS

| | | | |
|---|---|---|---|
| 2,910,978 | 11/1959 | Urist | 3/1.912 X |
| 2,998,990 | 9/1961 | Plattsmier et al. | 403/353 X |
| 3,002,466 | 10/1961 | Read | 403/353 X |
| 3,003,399 | 10/1961 | Donner | 29/149.5 B X |
| 3,192,868 | 7/1965 | Wahlmark | 403/122 X |
| 3,493,252 | 2/1970 | Watson et al. | 29/149.5 B X |
| 3,506,982 | 4/1970 | Steffee | 128/92 C X |
| 3,608,096 | 9/1971 | Link | 3/1.912 |
| 3,656,184 | 4/1972 | Chambers | 128/92 C X |
| 3,795,922 | 3/1974 | Herbert et al. | 3/1.911 |
| 3,829,904 | 8/1974 | Ling et al. | 3/1.912 |
| 3,869,729 | 3/1975 | Attenborough | 128/92 C X |
| 3,871,782 | 3/1975 | Johansson et al. | 403/353 X |
| 4,135,517 | 1/1979 | Reale | 3/1.913 X |

FOREIGN PATENT DOCUMENTS

| | | | |
|---|---|---|---|
| 2531080 | 2/1976 | Fed. Rep. of Germany | 3/1.911 |
| 192639 | 8/1937 | Switzerland | 403/123 |
| 767877 | 2/1957 | United Kingdom | 403/122 |

*Primary Examiner*—Clifford D. Crowder
*Attorney, Agent, or Firm*—Spencer & Kaye

[57] ABSTRACT

An endoprosthesis composed of a first member constituting a prosthesis socket provided interiorly with a chamber presenting a receiving surface, a second member constituting a prosthesis head arranged to be inserted into the socket to be received in the chamber and presenting a surface engaging the receiving surface when the head is received in the chamber, and a shaft firmly connected to the head. The head is arranged to be inserted into the socket by insertion movement, relative to the socket, from an insertion position to an inserted position, and to be rotated, relative to the socket, between the inserted position and an installed state. The socket presents a boundary edge formed to present at least one corner which encloses the head when the head is in the installed state and which defines a deformation, and the surface of the head is provided with a groove extending in the direction toward the shaft and defining a deformation, the depth of the groove being approximately equal to the constriction presented to the insertion opening by the corner.

10 Claims, 19 Drawing Figures

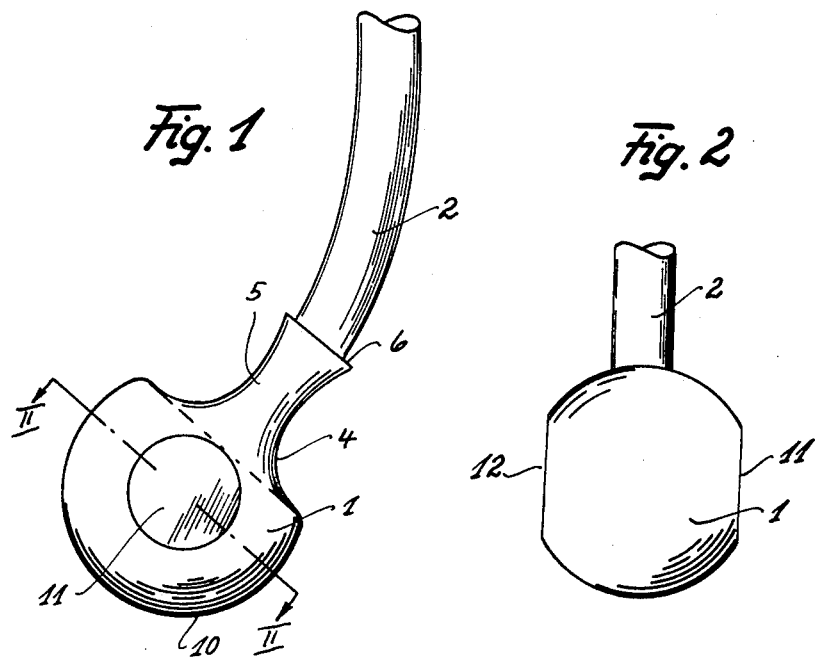

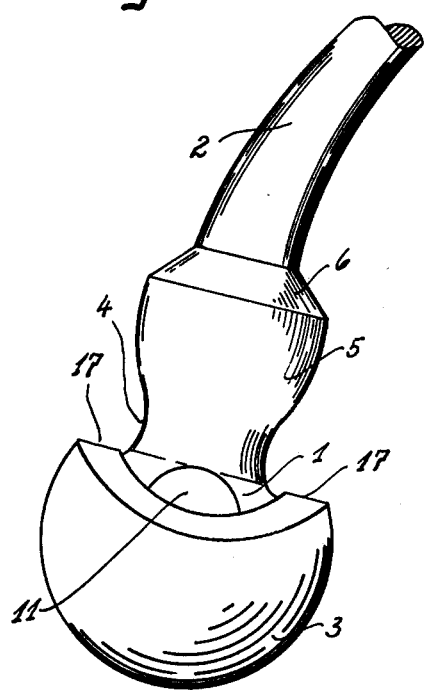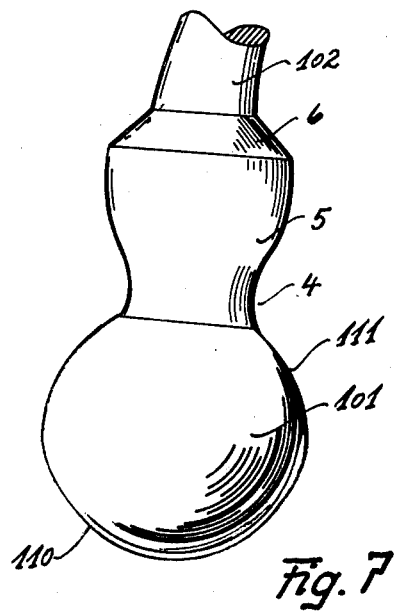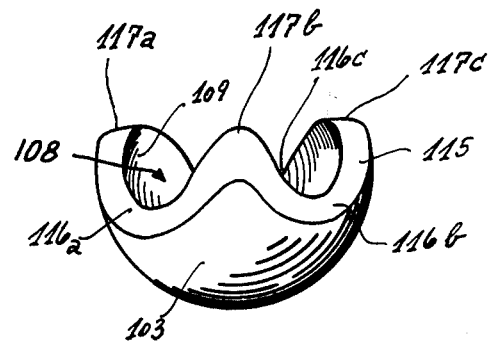

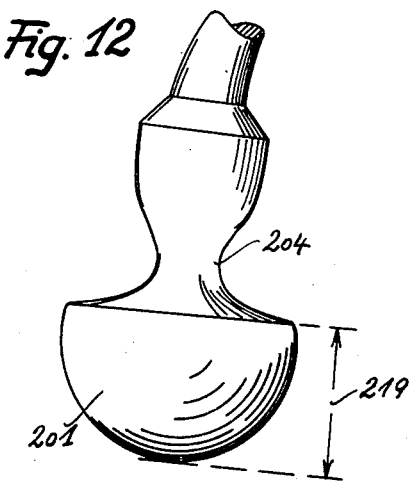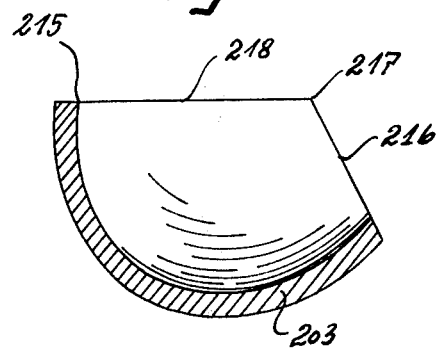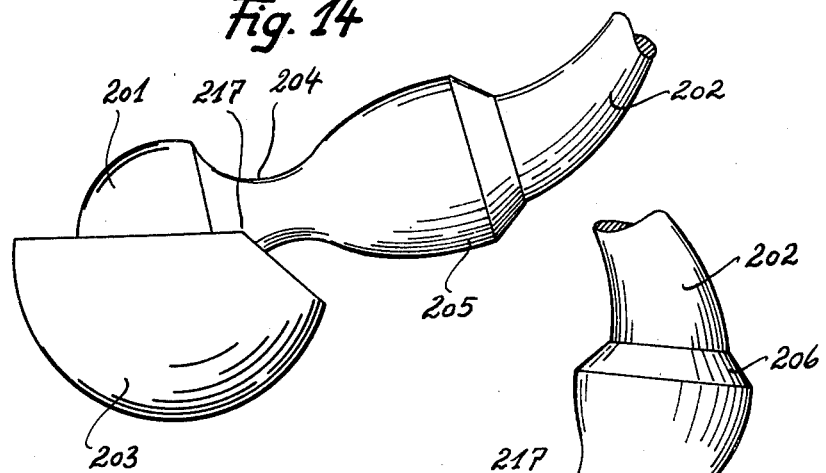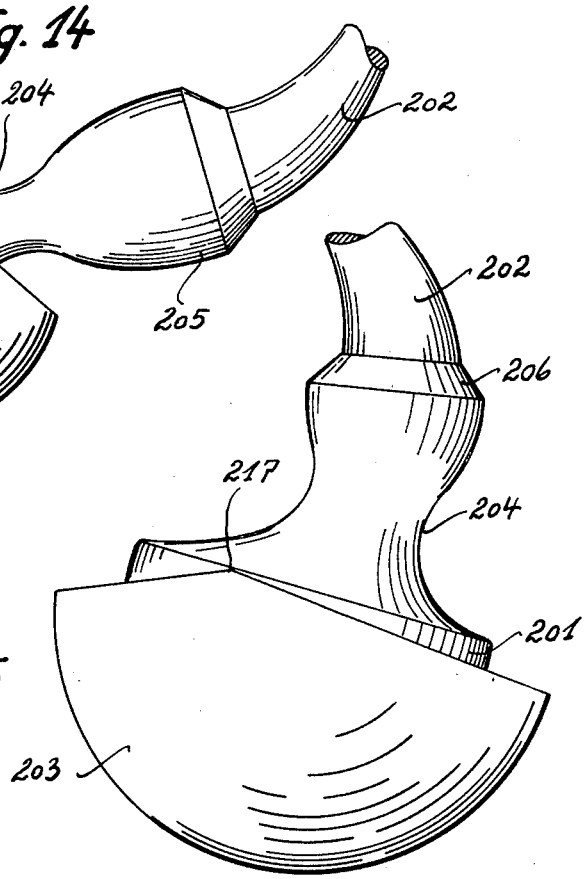

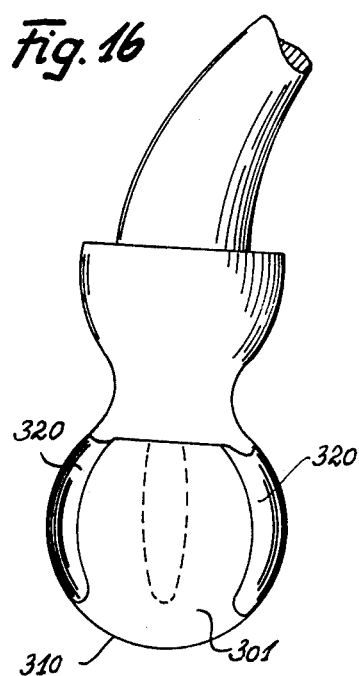
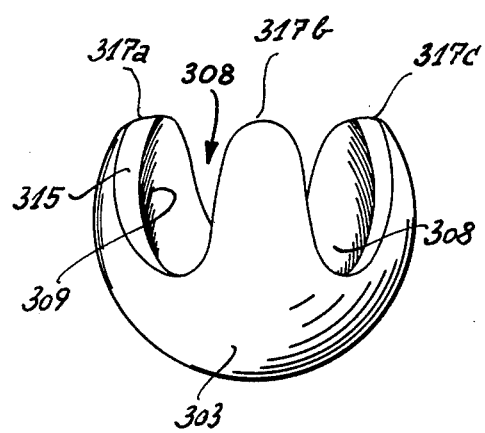
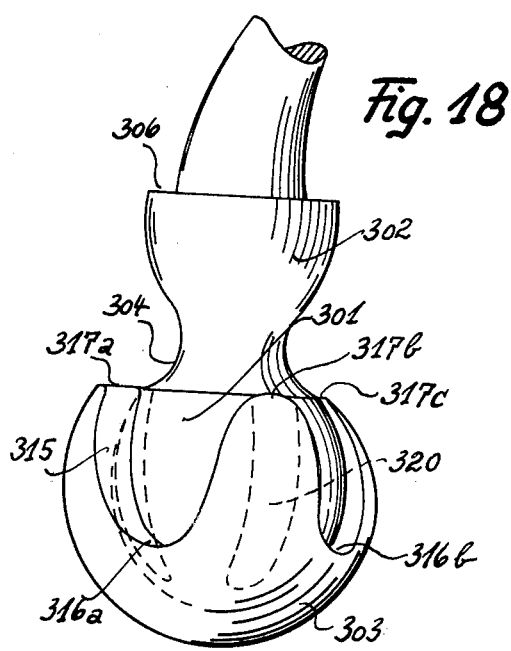
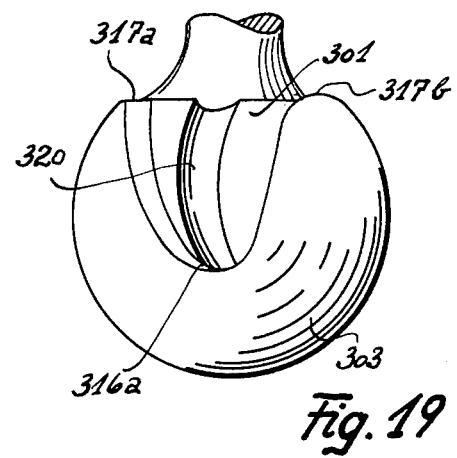

ENDOPROSTHESIS COMPOSED OF A SOCKET AND A HEAD RECEIVABLE AND LOCKABLE IN THE SOCKET

BACKGROUND OF THE INVENTION

The invention relates to an endoprosthesis, particularly as a replacement for shoulder and hip joints, comprising a prosthesis socket and prosthesis head firmly connected with a shaft, the surface of the prosthesis head engaging the surface of a chamber provided in the interior of the prosthesis socket to accommodate the prosthesis head.

Such endoprostheses may possibly prove difficult to install if the prosthesis head fits too tightly in the prosthesis socket. Under the influence of the tension generated by the ligaments and muscles, it is often difficult to bring the prosthesis head into its correct position if it is to be inserted into the prosthesis socket with a tight fit.

For this reason and to increase the freedom of movement of the prosthesis head in the prosthesis socket, it is known to enlarge the insertion opening provided in the prosthesis socket. With this measure, it becomes possible to substantially increase the freedom of movement of the prosthesis head in the prosthesis socket. However, there exists the danger that when the prosthesis socket is not in quite the proper position the prosthesis head will inadvertently pop out so that it must be reinserted in the prosthesis seat by a physician.

SUMMARY OF THE INVENTION

It is therefore the object of the present invention to improve an endoprosthesis of the above mentioned type so that the prosthesis head can be inserted into the prosthesis socket without difficulty and without thereby creating the danger that the prosthesis head may inadvertently pop out of the prosthesis socket.

This problem is solved according to the invention in that the chamber located in the interior of the prosthesis socket is provided with an insertion opening which corresponds to the dimensions of the prosthesis head when in the insertion position and which, in the position taken by the prosthesis head and prosthesis socket when the entire prosthesis is in the installed state, is locked in by the shape of at least one of the mutually engaging prosthesis members.

With this design of the endoprosthesis it is possible to design the insertion opening in such a way that the prosthesis head can be easily inserted into the prosthesis socket even if the prosthesis socket is not in the proper position. Moreover, the design of the insertion opening additionally provides good mobility of the prosthesis head within the prosthesis socket. On the other hand, by locking the prosthesis head with respect to the prosthesis socket it is accomplished that the prosthesis head cannot pop out of the prosthesis socket even under extreme deflections. The lock is effected by designing either the prosthesis socket or the prosthesis head or both members so that both parts are easily movable with respect to one another without there existing the danger, in the case of extreme deflections, that the two parts contact one another.

According to a preferred embodiment of the invention, once the prosthesis head has been rotated with respect to the prosthesis socket to assume the installed position, the insertion opening is locked. Since the prosthesis socket is firmly connected with the bone, rotation of the prosthesis head with respect to the prosthesis socket is easier than if the prosthesis socket must be rotated into its position with respect to the bone in order to lock it. By skillfully inserting the shaft and thus the prosthesis head into the femur or the humerus, respectively, the prosthesis head can be inserted into the prosthesis socket in the unlocked position. Then the femur or humerus, respectively, is brought into a position by means of rotation in which it is used most frequently in its natural way. In this position, the prosthesis head is locked with respect to the prosthesis socket so that the prosthesis head cannot slide out of the prosthesis socket even under great deflections.

BRIEF DESCRIPTION OF THE DRAWINGS

Further details of the invention will become evident from the detailed description that follows and from the attached drawings in which preferred embodiments of the invention are illustrated in an exemplary manner. The drawings show in:

FIG. 1, a side view of a prosthesis head with shaft inserted and flattened portions at both sides;

FIG. 2, a sectional view of a prosthesis head with flattened portions at the sides, taken along line II—II of FIG. 1;

FIG. 3, a top view of a prosthesis socket with flattened inner surfaces;

FIG. 4, a longitudinal sectional view of a prosthesis socket according to section line IV—IV of FIG. 3;

FIG. 5, a cross section of a prosthesis socket with flattened inner walls;

FIG. 6, a composite drawing of a prosthesis head inserted into a prosthesis socket;

FIG. 7, a side view of a prosthesis head having two different diameters;

FIG. 8, a side view of a prosthesis socket having an edge provided with a plurality of corners;

FIG. 12, a side view of a prosthesis head designed in the form of a spherical calotte;

FIG. 13, a section through a prosthesis socket having an insertion opening which is adapted to the spherical calotte;

FIG. 14, a side view of a prosthesis head placed in an oblique orientation for insertion into the hip socket;

FIG. 15, a side view of a prosthesis head pivoted into the installed position;

FIG. 16, a side view of a prosthesis head with grooves formed in its surface;

FIG. 17, a side view of a prosthesis socket having three corners in its edge;

FIG. 18, a side view of a prosthesis head in the insertion position; and

FIG. 19, a side view of a prosthesis head inserted into the prosthesis socket and rotated into the installed position.

DESCRIPTION OF THE PREFERRED EMBODIMENTS

Figure 9:
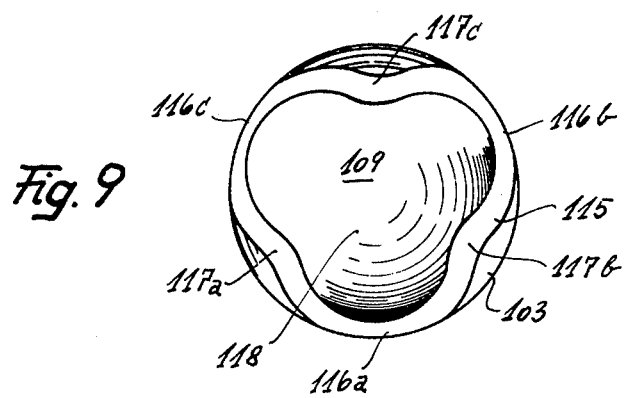
FIG. 9, a top view of the prosthesis socket according to FIG. 8.
Figure 10:
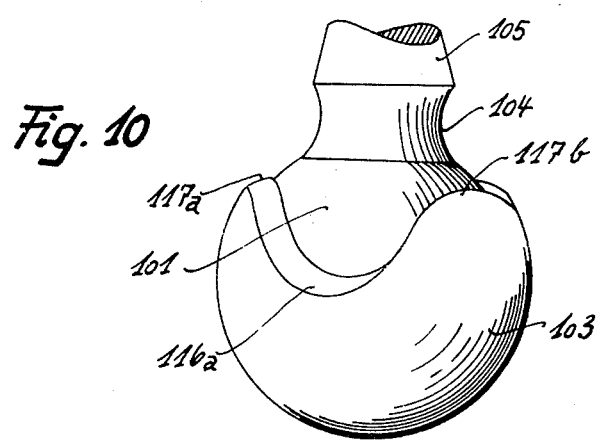
FIG. 10, a side view of a prosthesis head inserted into a prosthesis socket.

An endoprosthesis essentially comprises, as shown in FIGS. 1-6, a prosthesis head 1, a shaft 2 and a prosthesis socket 3. The prosthesis head 1 is essentially spherical in design. At its transition to the shaft 2 a constriction forms the prosthesis neck 4. This neck widens, as shown in FIG. 6, into a transition piece 5 which constitutes the transition from prosthesis head 1 to shaft 2. In this piece there already exists a deflection from the direction of orientation of the prosthesis neck 4 to that of the shaft 2. At its junction with the transition piece 5, the neck is surrounded by a collar 6 formed by the transition piece 5, the collar serving as abutment for the femur or humerus, respectively, which is connected to the transition piece 5.

The prosthesis socket is essentially designed as a hollow hemisphere whose outer surface is inserted into a bearing which has been correspondingly prepared in surgery. The interior of the prosthesis socket 3 is provided in the form of a chamber 8 whose inner surface 9 is essentially spherical in design. The surface 10 of the prosthesis head 1 engages the inner surface 9 after the endoprosthesis has been installed.

At two diametrally opposed locations, the surface 10 of the prosthesis head 1 has flattened portions 11, 12 which are coplanar with one another and with the plane defined by the curvature of the shaft 2.

The inner surface 9 has corresponding flattened portions 13, 14. These are also coplanar to one another. Their spacing corresponds to the spacing of the flattened portions 11, 12 so that the prosthesis head 1 with its flattened portions 11, 12 can be inserted into chamber 8 with a good fit. The prosthesis socket 3 has a delimiting edge 15 of a thickness corresponding to the wall thickness of the prosthesis socket 3. This edge 15 extends essentially on a diametral line on the prosthesis socket 3 which has the shape of a sphere. Or, as shown in FIG. 5, the edge may be provided with an edge section 16 which extends at an obtuse angle to the remaining edge 15 and cuts a calotte-shaped section from the prosthesis socket 3. Due to this edge section 16, there are formed in the region of edge 15 two opposing corners 17 from which the edge 15, on the one hand, and the edge section 16, on the other hand, drop obliquely downwardly when the prosthesis socket rests on its outer surface 7.

Expediently, the flattened portions 13, 14 are provided in the region of these corners 17 since, even after flattening, they will overlap the surface 10 of the prosthesis head 1 with the required precision. In this way, the size of the force transmitting inner surface area 9 of the chamber 8 is not unduly reduced.

The installation of the endoprosthesis designed in this manner is effected in that initially the prosthesis socket 3 is placed into the location which has been prepared for this purpose. In order to realize as much freedom of movement as possible for the prosthesis head with respect to the prosthesis socket, the prosthesis socket 3 is inserted in such a manner that its corners 17 protrude toward piece 5 when the head 1 is installed, as shown in FIG. 6. However, corners 17 will not unnecessarily impede the movement of the femur or humerus, respectively, since the major direction of that movement is parallel to the planes defined by flattened portions 13 and 14, as can also be seen in FIG. 6.

Then the shaft 2 is introduced into the surgically prepared marrow cavity of the receiving bone and is fastened there. In this way, the shaft 2 and thus the prosthesis head 1 are given a fixed association in the direction of the bone and thus in the direction of its movement. This also fixes the direction of the planes defined by the flattened portions 11, 12 with respect to the direction of movement of the bone. These flattened portions extend essentially perpendicularly to the plane defined in the main direction of bone movement.

Then the prosthesis head 1 is inserted into the prosthesis socket 3. During insertion, the bone is brought into a position where the flattened portions 11, 12 are associated with the flattened portions 13, 14. This position does not coincide with the main direction of movement of the bone; it is taken only for purposes of inserting the prosthesis head 1 into the prosthesis socket 3.

Then the bone is rotated into the initial position which corresponds to its main direction of movement, as shown in FIG. 6. Thus the prosthesis head 1 is simultaneously rotated into a position with respect to the prosthesis socket 3 in which the flattened portions 11, 12 no longer lie in the same plane as the flattened portion 13, 14. The flattened portions 11, 12 of the prosthesis head 1 are collared by the inner surface 9 of chamber 8 so that in this position the prosthesis head 1 can no longer slide out of the prosthesis socket 3. The corners 17 then overlap the prosthesis head 1 at a nonflattened location so that care is taken that the surface 10 of prosthesis head 1 rests securely on the inner surface 9 of chamber 8. The insertion opening 18 disposed between the flattened portions 13, 14 is locked in this manner. Such locking is also possible with a prosthesis socket 3 which does not have an edge section 16. Finally, it is also possible to provide, instead of corners 17, other protrusions on edge 15 to lock the prosthesis head 1 in the prosthesis socket 3.

According to another embodiment of the invention, shown in FIGS. 7-11, the prosthesis head 101 may have a design in which surfaces of spheres having different diameters are combined. While the surface 110 corresponding to the larger sphere engages the inner surface 109 of the prosthesis socket 103 in the main direction of load of the installed endoprosthesis, the surface corresponding to the sphere with the smaller diameter 111 serves to insert the prosthesis head 101 into the chamber 108 of the prosthesis socket 103. For this purpose the edge 115 is provided with three edge sections 116a, 116b and 116c. In this way, three corners 117a, 117b, 117c are formed in the course of edge 115. Between these corners 117a, 117b, 117c extends the surface 109 of chamber 108 which is in engagement with the larger diameter surface 110 of the prosthesis head 101 inserted into the prosthesis socket 103. The three corners 117a, 117b and 117c define between them the insertion opening 118 through which the prosthesis head 101 is inserted into the chamber 108 with its smaller diameter surface 111.

Figure 11:
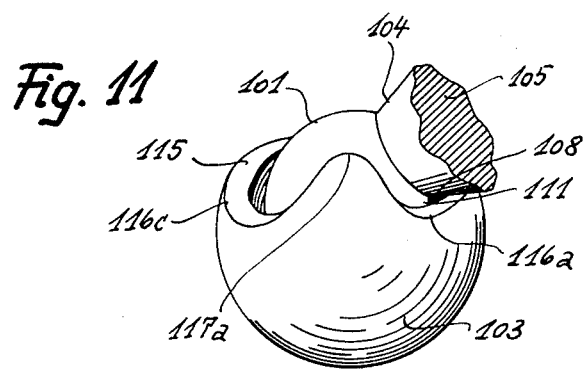
FIG. 11, a side view of a prosthesis head which has been put into an oblique position for the purpose of removing it from the prosthesis socket.

For this purpose, the prosthesis head 101 is rotated so that one of the corners 117a projects into the prosthesis neck 104, as shown in FIG. 11. Then the insertion opening 118 defined by the edge section 116b opposite corner 117a corresponds to the cross section of the sphere having the smaller diameter 111. In this position, the prosthesis head 101 can be placed into the insertion opening 118 and subsequently pivoted into the installed position shown in FIG. 10. In this way, the larger diameter surface 110 of prosthesis head 101 enters the chamber 108 and engages its inner surface 109. In this position, the three corners 117a, 117b and 117c grip the prosthesis head 101 with their inner surfaces facing the chamber 108 to such an extent and so snugly, that the prosthesis head 101 cannot slide back out of the insertion opening 118. In this way, the prosthesis head 1 is locked in the prosthesis socket 103 in the main direction of movement. Moreover, the facing surfaces 110 and 109 engage one another over a large area so that only slight areal pressures can occur.

In principle, such a lock is also possible by means of a prosthesis socket 103 which has, as shown in FIG. 11, a smooth edge 115 or less than three corners 117a, 117b and 117c. In that case, it is merely necessary to correspondingly vary the ratio between the surfaces having the larger diameter 110 and those having the smaller diameter 111. It is, moveover, conceivable to also select more than three corners.

In any case, it is expedient to arrange the surface 110 corresponding to the larger diameter in the sense of the path of the lines of force with respect to the opening of the shaft 102 into the prosthesis head 101. In this way, the force is transmitted in the region of lower areal pressures.

Of advantage but not necessary is a selection of the surface having the smaller diameter 111 under consideration of the prosthesis neck 104. Due to the expedient design of the prosthesis neck 104, the diameter of the prosthesis head is shorter in the direction of the prosthesis neck 104 than the diameter perpendicular thereto.

According to a further embodiment of the invention, shown in FIGS. 12–15, the prosthesis head 201 is provided in the form of a spherical calotte, whose height 219 can be adapted to the respectively available insertion opening 218. This insertion opening 218 is formed by the edge 215 of the prosthesis socket 203. This edge 215 is formed in such a manner that an edge section 216 forms an obtuse angle with the edge 215. The edge section 216 is here placed in such a manner that the prosthesis neck 204 projects into it and the opening formed by the remaining edge 215 has approximately the same height as the height 219, the height of the opening being measured from the merging line of the edge section 216 to the edge 215 opposite that line. On the basis of the edge section 216, it is possible to insert the prosthesis head 201, as shown in FIG. 14, in such a manner that the major direction of the prosthesis head 201 extends obliquely to the final installed position. After the prosthesis head 201 has been inserted into the prosthesis socket 203 in this way, it is subsequently placed upright into the main direction of movement shown in FIG. 15 in which the main loads are transferred from the prosthesis head 201 to the prosthesis socket 203. The prosthesis socket 203 is here expediently installed in such a manner that the edge section 216 is in a forward orientation. In this way, the corners 217 formed by the edge section 216 are not in the way of the major movements performed by the prosthesis head 201. On the other hand, these corners 217 collar the prosthesis head 201 in its spherical calotte-shaped design so that the prosthesis head cannot pop out of the prosthesis socket 203 during the performance of the major movements.

Expediently, the portion of the edge 215 remaining after formation of the edge section 216 is greater than the edge section 216. In this way, it is possible to adapt the height 219 to the corresponding height of the remaining edge. The greater this height 219, the greater is the surface remaining available on the prosthesis head 201 for the transmission of force.

Finally, according to a further embodiment of the invention shown in FIGS. 16–19, it is conceivable to provide grooves 320 in the prosthesis head 301 to extend in the direction of insertion of the prosthesis head 301 into the prosthesis socket 303. Corners 317a, 317b, 317c formed in the edge 315 of the prosthesis socket 303 engage in these grooves 320, as shown in FIG. 18. These corners 317a, 317b, 317c delimit the inner surface 309 of the chamber 308. The position of the grooves 320 on the surface 310 of the prosthesis head 301 with respect to the corners 317a, 317b, 317c is here arranged so that after insertion of the prosthesis head 301 into chamber 308 and pivoting the prosthesis head in the major direction of movement, the grooves 320 are moved out of the range of corners 317a, 317b, 317c, as shown in FIG. 19. In this way, it is prevented that during performance of the major movements the corners 317a, 317b, 317c can enter into grooves 320. In this way, the prosthesis head 301 is locked in its position in the prosthesis socket 303 corresponding to the major direction of movement.

Expediently, the correct insertion of the prosthesis head 301 in the prosthesis socket 303 is facilitated by an asymmetrical arrangement of corners 317a, 317b, 317c as well as of grooves 320. In this way, the prosthesis head 301 can be inserted into the prosthesis socket 303 only in a quite defined position which corresponds to the arrangement of corners 317a, 317b and 317c on the one hand and of grooves 320 on the other hand. It is then possible without difficulty to pivot the prosthesis head 301 from this position into the position corresponding to the major direction of movement.

Instead of three corners 317a, 317b, 317c, an edge 315 having a different shape can also be used for this type of lock. For example, merely one corner is sufficient for alignment and locking of the prosthesis head 301 in the prosthesis socket 303. In such a case the edge 315 must be designed correspondingly.

The grooves 320 in the prosthesis head 301 are designed in dependence on the expedient manner of insertion of the prosthesis head 301 into the prosthesis socket 303. With straight-line insertion in the direction of the diameter of the prosthesis head 301, the grooves are also linear, essentially in the direction of the meridian of the spherical prosthesis head 301. Since the mutual spacing between the corners 317a, 317b, 317c is constant, the grooves 320 are deepest in the area of the largest diameter of the prosthesis head 301 while they are shallow at the end near the surface in the area of the prosthesis neck 304 and of the surface 310 of the prosthesis head 301 opposite the prosthesis neck.

The position of the grooves 320 is expediently so selected that, in the major direction of movement of the bone, they do not extend in the zone of transmission of the major forces. Moreover, grooves 320 may also extend obliquely to the diameter line or in a helical line on the surface 310 of the prosthesis head 301, depending on the manner in which the prosthesis head 301 can be inserted most favorably into the prosthesis socket 303. If, for example, it is inserted into the socket in a screw-like manner, the grooves 320 on the surface 310 of the prosthesis head 301 extend like a screw thread, as depicted in FIG. 19.

If only one corner is provided to guide the prosthesis head 301 in the prosthesis socket 303, this corner is made relatively strong so that the groove 320 must be made correspondingly wide and deep. However, it is also possible, when there are a plurality of corners 317, to make the corner disposed in the region of the transfer of the major weight stresses stronger than the other corners. In this case as well, the design of the groove 320 must be adapted to the shape of the corresponding corner 317.

I claim:

1. In an endoprosthesis composed of a first member constituting a prosthesis socket provided interiorly with a chamber presenting a receiving surface, a second member constituting a prosthesis head arranged to be inserted into the socket to be received in the chamber and presenting a surface engaging the receiving surface when the head is received in the chamber, and a shaft firmly connected to the head, the improvement wherein: said head is arranged to be inserted into said socket by insertion movement, relative to said socket, from an insertion position to an inserted position, and to be movable, relative to said socket, between the inserted position and an installed state; said head and socket are constructed such that movement between the inserted position and the installed state is effected by rotation of said head relative to said socket; said chamber presents an insertion opening corresponding in configuration to said head when said head is in the insertion position; at least one of said members is shaped for locking said head in said socket when said head is in the installed state; said surfaces of said head and said socket have mutually matched, approximately spherical forms and are provided with deformations which mate with one another only when said head is in the inserted position relative to said socket; said socket presents a boundary edge formed to present at least one corner which encloses said head when said head is in the installed state and which defines one said deformation with which said socket is provided, said corner extending in the direction toward said shaft to a location beyond the plane of maximum width of said head, perpendicular to the direction of insertion movement, when said head is in its inserted position, and said surface of said head is provided with a groove extending in the direction toward said shaft and defining one said deformation with which said head is provided, the depth of said groove being approximately equal to the constriction presented to said insertion opening by said corner.

2. An article as defined in claim 1 constructed as a replacement for a shoulder or hip joint.

3. An article as defined in claim 1 wherein said groove is located outside of the portion of said surface of said head which, under normal loading of said endoprosthesis, engages said receiving surface of said chamber.

4. An article as defined in claim 3 wherein said head is provided with a constriction in the region where it is connected to said shaft, which constriction constitutes a prosthesis neck, and said groove begins at said constriction and extends toward the extremity of said head surface remote from said constriction.

5. An article as defined in claim 4 wherein said groove extends in a straight line along a diametral plane of said head.

6. An article as defined in claim 4 wherein said groove extends obliquely to a diametral plane of said head and has the form of a screw thread.

7. An article as defined in claim 4 wherein said boundary edge presents a plurality of said corners, said surface of said head is provided with a plurality of said grooves each associated with a respective corner, and said insertion opening is delimited by said corners and the portions of said edge extending between said corners.

8. An article as defined in claim 7 wherein said corners are distributed asymmetrically around said boundary edge.

9. An article as defined in claim 8 wherein said grooves are located in regions which lie outside of the portions of said surface of said head which transmit major weight stresses when said endoprosthesis is installed.

10. An article as defined in claim 9 wherein one of said corners is located at a position around said boundary edge where a high level of force transmission occurs during use of said endoprosthesis, said one corner is formed to be of higher strength than the others of said corners, said others of said corners serve as guide corners, and each said groove is adapted and shaped to a respective one of said corners.

* * * * *